(12) United States Patent
Bowden et al.

(10) Patent No.: US 6,316,624 B1
(45) Date of Patent: Nov. 13, 2001

(54) PROCESS FOR THE PREPARATION OF SUBSTITUTED 8-AZABICYCLO[3,2,1] OCTANES

(75) Inventors: Martin Charles Bowden; Stephen Martin Brown, both of Huddersfield (GB)

(73) Assignee: Syngenta Ltd. (GB)

( * ) Notice: Subject to any disclaimer, the term of this patent is extended or adjusted under 35 U.S.C. 154(b) by 0 days.

(21) Appl. No.: 09/555,429

(22) PCT Filed: Dec. 7, 1998

(86) PCT No.: PCT/GB98/03635

§ 371 Date: May 30, 2000

§ 102(e) Date: May 30, 2000

(87) PCT Pub. No.: WO99/29691

PCT Pub. Date: Jun. 17, 1999

(30) Foreign Application Priority Data

Dec. 9, 1997 (GB) .................................................. 9726033

(51) Int. Cl.$^7$ ...................... C07D 451/02; C07D 451/04
(52) U.S. Cl. ...................... 546/125; 546/124; 546/132
(58) Field of Search ........................... 546/124, 125, 546/132

(56) References Cited

U.S. PATENT DOCUMENTS 3,120,537    2/1964   Archer et al. ...................... 546/132

FOREIGN PATENT DOCUMENTS

96/37494   11/1996   (WO) .
97/13770    4/1997   (WO) .
97/43286   11/1997   (WO) .

OTHER PUBLICATIONS

G.A. Olah, Synthetic Methods and Reactions; 60'. Improved One–Step Conversion of Aldehydes into Nitriles with Hydroxylamine in Formic Acid Solution, Synthesis, 112–113 (1979).

M. Fishman et al., Studies in Alkylation, 5 J.Heterocyclic Chem., 467–469 (Aug. 1968).

P. Bartlett et al., Chorismate Mutase Inhibitors: Synthesis and Evaluation of Some Potential Transition–State Analogues, 53 J. Org. Chem., 3195–3210 (1988).

Paquette, L., Encyclopedia of Reagents for Organic Synthesis, 2792 (1995).

Houben–Weyl, Methoden der Organischen Chemie, G. Thieme, 1339–1346 (1988).

Houben–Weyl, Methoden der Organischen Chemie, G. Thieme, 549–555 (1983).

*Primary Examiner*—Alan L. Rotman
(74) *Attorney, Agent, or Firm*—Hale and Dorr, LLP

(57) ABSTRACT

A process for preparing a compound of formula (IV) wherein $R^1$ is $C_{1-4}$ alkyl, $C_{1-4}$ haloalkyl, benzyl, $C_{3-6}$ alkenyl or $C_{3-6}$ alkyny, (provided that the α-carbon atom of $R^1$ is neither unsaturated nor substituted with halogen), which comprises reacting a compound of formula (III) with a source of hydroxylamine in the presence of an acid. Compounds of formula (IV) are agrochemical intermediates.

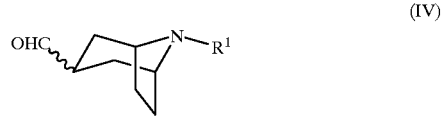

(IV)

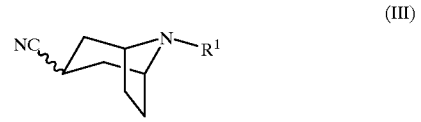

(III)

5 Claims, No Drawings

PROCESS FOR THE PREPARATION OF SUBSTITUTED 8-AZABICYCLO[3,2,1] OCTANES

CROSS-REFERENCE

This application is a 371 of PCT/GB98/03635 filed Dec. 27, 1998.

The present invention concerns a process for preparing 3-cyano-8-substituted-8-azabicyclo[3.2.1]octanes. 3-Cyano-8-substituted-8-azabicyclo[3.2.1]octanes are useful as intermediates for certain insecticides (see, for example, WO 96/37494).

The present invention provides a process for preparing a compound of formula (IV), wherein $R^1$ is $C_{1-4}$ alkyl, $C_{1-4}$ haloalkyl, benzyl, $C_{3-6}$ alkenyl or $C_{3-6}$ alkynyl (provided that the α-carbon atom of $R^1$ is neither unsaturated nor substituted with halogen), which comprises reacting a compound of formula (III) with a source of hydroxylamine in the presence of an acid. A preferred source of hydroxylamine is hydroxylamine hydrochloride or hydroxylamine itself. Suitable acids that can be used for this reaction include organic acids (such as formic acid or acetic acid) or mineral acids (such as hydrochloric acid, nitric acid or sulphuric acid).

In one particular aspect the present invention provides a process for preparing a compound of formula (IV), wherein $R^1$ is as defined above, comprising the steps:
 i. ring opening a compound of formula (II) to give a compound of formula (III); and,
 ii. reacting a compound of formula (III) with a source of hydroxylamine in the presence of an acid.

It is preferred that the ring opening of a compound of formula (II) is by reacting it with a strong organic acid (such as trifluoroacetic acid).

In another aspect the present invention provides a process for preparing a compound of formula (IV), wherein $R^1$ is as defined above, comprising the steps:
 i. converting a compound of formula (I) to a compound of formula (II) by a methylene insertion reaction;
 ii. ring opening a compound of formula (II) to give a compound of formula (III); and,
 iii. reacting a compound of formula (III) with a source of hydroxylamine in the presence of an acid.

It is preferred that the compound of formula (I) is converted to a compound of formula (II) by reacting it with a suitable sulphur ylid (such as that generated by reacting trimethylsulphoxonium iodide and an alkali metal hydride (for example sodium hydride)).

Alkyl groups may be straight or branch chains are, for example, methyl ethyl, n-propyl or iso-propyl.

Haloalkyl is preferably alkyl optionally substituted with chlorine or fluorine and is, for example, 2,2,2-trifluoroethyl or 2,2-difluoroethyl.

Alkenyl and alkynyl groups are, for example, allyl or propargyl.

A compound of formula (II) can be prepared by adding a compound of formula (I) to a sulphur ylid (such as the ylid formed by the reaction of sodium hydride with trimethylsulphoxonium iodide), the reaction being carried out in a suitable solvent (such as tetrahydrofuran) and at a suitably elevated temperature (preferably in the range 50–100° C., such as at the boiling point of the solvent used).

A compound of formula (III) can be prepared by ring opening a compound of formula of formula (II) under acidic conditions (such as with an organic acid (preferably acetic acid or, especially, trifluoroacetic acid) or a suitable ion exchange resin (for example an Amberlyst® resin)) in a suitable solvent (such as toluene) and at a suitably elevated temperature (such as between 50° C. and the boiling point of the solvent used).

A compound of formula (IV) can be prepared by reacting a compound of formula (III) with hydroxylamine hydrochloride in the presence of an acid, which may also act as a solvent (such as formic acid) at a suitably elevated temperature (such as between 50° C. and the boiling point of the solvent used).

In another aspect the present invention provides a process for preparing a compound of formula (IV) which comprises the steps:
 i. reacting a compound of formula (I) with a sulphur ylid (preferably formed by the reaction of sodium hydride with trimethylsulphoxonium iodide) at 50–100° C. to give a compound of formula (II);
 ii. ring opening a compound of formula (II) under acidic conditions and at a temperature in the range 50–120° C. to give a compound of formula (III); and,
 iii. reacting a compound of formula (III) with hydroxylamine hydrochloride in the presence of an acid and at a temperature in the range 50–120° C.

A compound of formula (A) can be prepared by reacting a compound of formula (IV) with a compound $R^2L$, wherein $R^2$ is pyridyl optionally substituted with halogen, $C_{1-4}$ alkyl, $C_{1-4}$ alkoxy, cyano, $C_{2-4}$ alkenyl or $C_{2-4}$ alkynyl, and L is a suitable leaving group (such as halogen or mesylate). Thus, in a further aspect the present invention provides a compound of formula (A) when made by reacting a compound of formula (IV) (as prepared by a process as hereinbefore described) with a compound $R^2L$.

A compound of formula (A), wherein $R^1$ is $C_{1-4}$ alkyl, $C_{1-4}$ haloalkyl, benzyl, $C_{3-6}$ alkenyl or $C_{3-6}$ alkynyl (provided that the β-carbon atom of $R^1$ is neither unsaturated nor substituted with halogen), and $R^2$ is pyridyl optionally substituted with halogen, $C_{1-4}$ alkyl, $C_{1-4}$ alkoxy, cyano, $C_{2-4}$ alkenyl or $C_{2-4}$ alkynyl, when prepared by a process comprising the steps:
 i. reacting a compound of formula (III) with a source of hydroxylamine in the presence of an acid to provide a compound of formula (IV); and,
 ii. reacting a compound of formula (IV) with a compound $R^2L$, wherein L is a suitable leaving group (such as halogen or mesylate).

In a further aspect the present invention provides a compound of formula (II) wherein $R^1$ is $CH_2CHF_2$ or $CH_2CF_3$.

In a still further aspect the present invention provides a compound of formula (III) wherein $R^1$ is $CH_2CHF_2$ or $CH_2CF_3$.

The following Example illustrate the invention. Selected NMR data and mass spectral data are presented in the Examples. For NMR data, no attempt has been made to list very absorption. The following abbreviations are used throughout the Examples:

| m = multiplet | ppm = parts per million |
|---|---|
| THF = tetrahydrofuran | q = quartet |
| s = singlet | |

EXAMPLE 1

This Example illustrates the preparation of 3-cyano-8-(2,2,2-trifluoroethyl)-8-azabicyclo[3.2.1]octane.

Step 1

A dry 500 ml 3-necked round bottom flask was fitted with a pressure equalised dropping funnel, nitrogen bubbler, thermometer, reflux condenser and mechanical stirrer. Sodium hydride (7.84 g, 0.32 mol) was charged to the reaction flask followed by trimethyl sulphoxonium iodide (71.7 g, 0.32 mol). Dry THF (200 ml) was charged to a dropping funnel and then added over 0.25 hour. The mixture was agitated at ambient for 0.5 hour, during which time hydrogen evolved gently. 8-(2,2,2-Trifluoroethyl)-8-azabicyclo[3.2.1]octan-3-one (50 g, 0.23 mol) in dry THF (50 ml) was added to the mixture after which the mixture was refluxed for 4 hours. After this time, the THF was removed by rotary evaporation, then saturated sodium metabisulphite (200 ml)) was added. Hexane (100 ml) was added and separated and the aqueous later was washed with hexane (2×100 ml). The organic extracts were combined, dried (MgSO$_4$) and evaporated in vacuo to give a crude sample of a compound of formula (II) wherein R$^1$ is CF$_3$CH$_2$ which was purified by distillation (58° C. @ 2 mmHg) to leave a colourless oil (36 g, 68% yield).

$^1$H NMR (CDCl$_3$): δ 1.10–1.25(m,2H), 1.85–2.15(m,4H), 2.35–5.50(m,2H), 2.45(s,2H), 2.95(q,2H), 3.30–3.40(m,2H) ppm.

$^{13}$C NMR (CDCl$_3$): δ 27(s), 39(s), 49(s), 55(q), 62(s), 66(s), 126(q)ppm.

Mass spectral data: 221 (M$^+$), 220, 192, 156, 150, 110.

Step 2

A 25 ml 3-necked round bottom flask was fitted with a reflux condenser, thermometer and magnetic stirrer and placed under a nitrogen atmosphere. The product of Step 1 (0.5 g, 2.1 mmol) and dry toluene (15 ml) were charged to the flask after which trifluoroacetic acid (0.33 ml, 4.2 mmol) was added dropwise. The reaction was agitated at room temperature for 1 hour and then refluxed for 1 hour. The reaction mass was cooled to ambient, dichloromethane (40 ml) was added and the mixture then washed with aqueous sodium bicarbonate (3×20 ml, 10%). The combined organics were dried (MgSO$_4$) and concentrated in vacuo to give 3-formyl-8-(2,2,2-trifluoroethyl)-8-azabicyclo[3.2.1]octane predominantly as the equatorial epimer (0.44 g, 54% yield). Purification by column chromatography (silica, 40/60 diethyl ether:hexane) gave 3-formyl-8-(2,2,2-trifluoroethyl)-8-azabicyclo[3.2.1]octane as a yellow solid.

$^1$H NMR (CDCl$_3$) δ 1.55–2.10(m,8H), 2.40–2.55(m,1H), 2.90(q,2H), 3.30–3.45(m,2H), 9.60(s,1H)ppm.

Mass spectral data: 221(M$^+$), 192, 156, 150, 110.

Step 3

To a 25 ml round bottom flask fitted with a reflux condenser, magnetic stirrer and a thermometer was charged formic acid (5 ml). The apparatus was filled with nitrogen. To this was charged 3-formyl-8-(2,2,2-trifluoroethyl)-8-azabicyclo([3.2.1]octane (0.235 g, 0.9 mmol) and hydroxylamine hydrochloride (0.083 g, 1.2 mmol) and the reaction mixture was refluxed for 1 hour. The reaction mixture was cooled to ambient, water was added (20 ml) and the mixture was then neutralised (with cooling) by the addition of saturated sodium bicarbonate solution (2 ml). The resulting mixture was extracted with diethyl ether (3×20 ml), and the combined organics were dried (MgSO$_4$) and concentrated by rotary evaporation to give the title compound predominantly as the equatorial isomer (0.178 g, 74% yield).

$^1$H NMR (CDCl$_3$): δ 1.50–2.15(m,8H), 2.65–2.85(m,1H), 2.85(q.2H), 3.30–3.40(m,2H)ppm.

Mass spectral data: 218(M$^+$), 199, 189, 164, 150.

EXAMPLE 2

This Example illustrates the preparation of 3-formyl-8-(2,2,2-trifluoroethyl)-8-azabicyclo[3.2.1]octane.

A 100 ml 3-necked round bottom flask was fitted with a reflux condenser, thermometer and magnetic stirrer and the apparatus was filled with nitrogen. A compound of formula (II) wherein R$^1$ is CF$_3$CH$_2$ (1.5 g, 6.5 mmol) and dry toluene (30 ml) were charged to the flask, followed by Amberlyst®-15 ion exchange resin (0.45 g). The reaction was stirred at room temperature for 1 hour and then refluxed for 5.5 hour. The reaction mass was cooled to 40° C. and filtered to remove the Amberlyst® resin. Concentration in vacuo gave the title product predominantly as the axial epimer (1.06 g, 49% yield). Purification by short-path distillation (0.7 mmHg, 56° C.) gave the title product as a colourless mobile oil (0.48 g, 26% yield).

EXAMPLE 3

This Example illustrates the preparation of 3-formyl-8-(2,2,2-trifluoroethyl)-8-azabicyclo[3.2.1]octane.

A 100 ml 3-necked round bottom flask was fitted with a reflux condenser, thermometer and magnetic stirrer and the apparatus was filled with nitrogen. A compound of formula (II) wherein R$^1$ is CF$_3$CH$_2$ (2.0 g, 8.2 mmol), dry toluene (40 ml), and acetic acid (1.0 g, 17 mmol) were charged to the flask and the reaction mixture was heated to reflux for 0.5 hour. The heat source was removed and trifluoroacetic acid (0.19 g, 1.6 mmol) added to the reaction (via syringe/septum under the surface of the liquid). The reaction mixture was refluxed for 0.75 hour before cooling to ambient. The reaction mass was poured slowly onto a stirred saturated, aqueous solution of sodium bicarbonate (150 ml), the pH was adjusted to 8 with further saturated, aqueous solution of sodium bicarbonate (50 ml) and the aqueous extracted with CH$_2$Cl$_2$ (3×50 ml). The combined organics were dried (Na$_2$SO$_4$), filtered, and concentrated in vacuo to give the title product predominantly as the equatorial epimer, as a red/brown sticky tar (1.7 g, 44% crude yield).

$^1$H NMR (CDCl$_3$): δ 1.55–2.10(m.8H), 2.40–2.55(m, 1H), 2.90(q,2H), 3.30–3.45(m,2H), 9.60(m, 1H)ppm.

Mass spectral data: 221 (M$^+$), 192, 156, 150, 110.

EXAMPLE 4

This Example illustrates the preparation of a compound of formula (II) wherein R$^1$ is CF$_3$CF$_2$.

tert-Butyl alcohol (2 ml) and water (1 ml) were added to dimethylsulphide (1.5 g, 23.6 mmol) in a 50 ml 3-necked flask, fitted with septum inlet and stirrer bar. This mixture was stirred at ambient temperature, with portionwise addition of dimethylsulphate (1.5 g, 11.8 mmol) neat via syringe over 10 minutes. A slight exotherm was observed during this addition, and the temperature was maintained between 20–25° C. with a cold water bath. The reaction mixture was stirred for 1 hour, then (2,2,2-trifluoroethyl)-8-azabicyclo [3.2.1]octan-3-one (2.5 g, 11.8 mmol, starting material) was added in one batch, along with portionwise addition of potassium hydroxide (1.32 g, 23 mmol) over 15 minutes, again maintaining the temperature between 20–25° C. As the potassium hydroxide dissolved, the mixture turned from yellow/orange to red. The mixture was stirred vigorously at ambient temperature for 19 hours after which time gc analysis showed 47% starting material remaining. Further dimethylsulphate (0.5 ml) and potassium hydroxide (0.5 g) were added to the reaction mixture, which was stirred at ambient for an additional 6 hours. The mixture was then diluted with water (10 ml), stirred for ½ hour, and the resulting emulsion extracted twice with toluene. The organic extracts were combined, washed three times with aqueous sodium chlorate, once with water and once with saturated brine, and they were then concentrated under reduced pressure to leave a yellow/orange liquid (1.9 g). Analysis (gc) showed this to include the title compound (41%), starting material (29%) and some unidentified by-products.

Chemical Formulae used in the Description

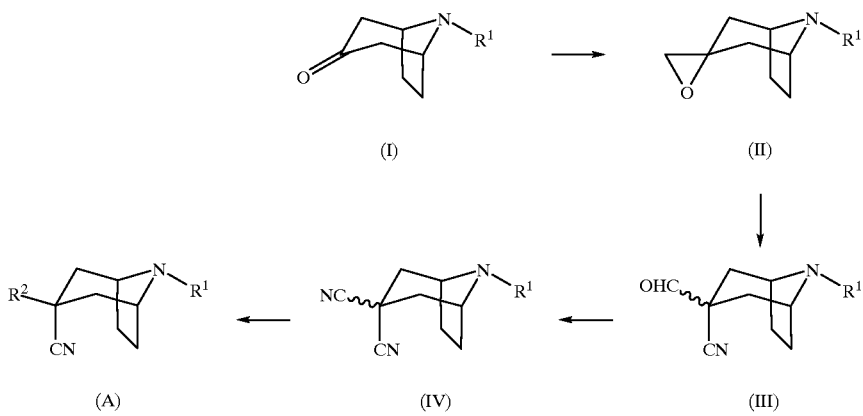

What is claimed is:

1. A process for preparing a compound of formula (IV):

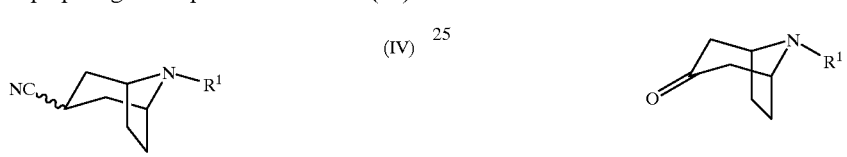

(wherein $R^1$ is $C_{1-4}$ alkyl, $C_{1-4}$ haloalkyl benzyl, $C_{3-6}$ alkenyl or $C_{3-6}$ alkynyl (provided that the α-carbon atom of $R^1$ is neither substrate nor substituted with halogen), which comprises:

i. ring opening a compound of formula (II):

under acidic conditions in the presence of an organic acid or an ion exchange resin, in a suitable solvent and at a temperature between 50° C. and the boiling point of the solvent used, to give a compound of formula (III):

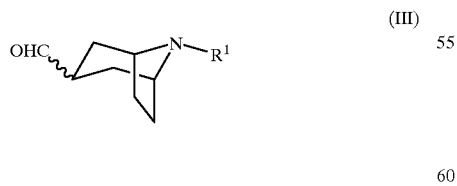

and, ii. reacting the compound of formula (III) with a source of hydroxylamine in the presence of an acid.

2. A process for preparing a compound of formula (IV) as claimed in claim 1 which comprises the steps:

i. converting a compound of formula (I):

(I)

wherein $R^1$ is as defined in claim 1, to a compound of formula (II) by a methylene insertion reaction;

ii. ring opening a compound of formula (II) under acidic conditions in the presence of an organic acid or an ion exchange resin, in a suitable solvent and at a temperature between 50° C. and the boiling point of the solvent used, to give a compound of formula (III); and, iii. reacting a compound of formula (III) with a source of hydroxylamine in the presence of an acid.

3. A process for preparing a compound of formula (IV) as claimed in claim 1 which comprises the steps:

i. reacting a compound of formula (I) with a sulphur ylid at 50–100° C. to give a compound of formula (II);

ii. ring opening a compound of formula (II) under acidic conditions in the presence of an organic acid or an ion exchange resin, in a suitable solvent and at a temperature in the range 50–120° C. to give a compound of formula (III); and, iii. reacting a compund of formula (III) with hydroxylamine hydrochloride in the presence of an acid and at a temperature in the range 50–120° C.

4. A process as claimed in claim 1, wherein $R^1$ is $CH_2CHF_2$ or $CH_2CF_3$.

5. A compound of formula (II) or (III):

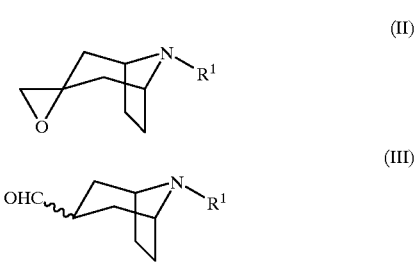

wherein $R^1$ is $CH_2CHF_2$ or $CH_2CF_3$.

* * * * *